US011524996B2

(12) United States Patent
Bhambure et al.

(10) Patent No.: US 11,524,996 B2
(45) Date of Patent: *Dec. 13, 2022

(54) METHOD FOR PRODUCING REFOLDED RECOMBINANT HUMANIZED RANIBIZUMAB

(71) Applicant: COUNCIL OF SCIENTIFIC & INDUSTRIAL RESEARCH, New Delhi (IN)

(72) Inventors: Rahul Sharad Bhambure, Pune (IN); Kayanat Mahammadtaki Gani, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 83 days.

This patent is subject to a terminal disclaimer.

(21) Appl. No.: 16/685,041

(22) Filed: Nov. 15, 2019

(65) Prior Publication Data

US 2020/0140535 A1 May 7, 2020

Related U.S. Application Data

(63) Continuation-in-part of application No. PCT/IN2018/050315, filed on May 18, 2018.

(30) Foreign Application Priority Data

May 19, 2017 (IN) .............................. 201711017654

(51) Int. Cl.
*C07K 16/22* (2006.01)
(52) U.S. Cl.
CPC .......... *C07K 16/22* (2013.01); *C07K 2317/24* (2013.01)
(58) Field of Classification Search
CPC ........................... C07K 16/22; C07K 2317/24
See application file for complete search history.

(56) References Cited

U.S. PATENT DOCUMENTS

2008/0125580 A1   5/2008   Pizarro et al.
2016/0289314 A1  10/2016   Shandlya et al.

FOREIGN PATENT DOCUMENTS

| CN | 102757496 A | 10/2012 |
| WO | WO9845331 | 10/1998 |
| WO | WO2013076657 | 5/2013 |
| WO | WO2014178078 | 11/2014 |
| WO | WO2016005931 | 1/2016 |

OTHER PUBLICATIONS

Nelson A. and Reichert J. Development trends for therapeutic antibody fragments. Nature biotechnology 2009, 27, No. 4.
Nelson A., Antibody fragments Hope and hype. MAbs, 2010, 2:1, 77-83.
Product insert and prescribing information for Lucentis.
EMEA scientific discussion, EMEA 2007 Website: http://www.ema.europa.eu/docs/en_GB/document_library/EPAR_-_Scientific_Discussion/human/000715/WC500043550pdf).
Lucentis Epar Product Information, Annex I. Summary of Product Characteristics.
Clark EDB., Protein refolding for industrial processes. Current Opinion in Biotechnology, 2001, 12(1): 202-207.
Jungbauer A., Kaar W., Current status of technical protein refolding. Journal of Biotechnology, 2007, 128(3): 587-596.
Middelberg APJ., Preparative protein refolding. Trends in Biotechnology, 2002, 20(10), 437-443.
Singh S. M., Panda A. K., Solubilization and refolding of bacterial inclusion body proteins. Journal of Bioscience and Bioengineering, 2005, 99(4), 303-310.
Hannig G. and Makrides S. Strategies for optimizing heterologous protein expression in *Escherichia coli*. Trends in Biotechnoigy, 1998, 16, 54-60.
Corisdeo S. and Wang B. Functional expression and display of an antibody Fab fragment in *Escherichia coli*: study of vector designs and culture conditions. Protein Expression and Purification 2004, 34, 270-279.
Humphreys D., Carrington B., Bowering L., Ganesh R., Sehdev M., Smith B., King L., Reeks D, Lawson A and Popplewell A. A plasmid system for optimization of Fab production in *Escherichia coli*: importance of balance of heavy chain and light chain synthesis, Protein Expression and Purification 2002, 26, 309-320.
O'Brien Ph., Maxwell G., and Campo M. Bacterial Expression and Purification of Recombinant Bovine Fab Fragments. Protein Expression and Purification 2002, 24, 43-50.
Carter P., Kelley R., Rodrigues M., Snedecor B., Covarrubias M., Velligan M., Wong W., Rowland A., Kotts C., Carver M., Yang M., Bourell J., Shepard H. and Henner D. High Level *Escherichia coli* Expression and Production of a Bivalent Humanized Antibody Fragment. Nature Biotechnology 1992, 10, 163-167.
BaneyxF. Recombinant protein expression in *Escherichia coli*. Current Opinion in Biotechnology, 1999,10, 411-421.
User protocol for transformation Novagen®.
Buchner J., Rudolph R., Renaturation, purification and characterization of recombinant Fab-fragments produced in *Escherichia coli*. Nature Biotechnology 1991, 9, 157-162.
Lilie H., Schwarz E., Rudolph R., Advances in refolding of proteins produced in *E. coli*. Current Opinion in Biotechnology 1998, 9, 497-501.
Bradford M., A rapid and sensitive method for the quantitation of microgram quantities of protein utilizing the principle of protein-dye binding. Analytical Biochemistry 1976, 72, 248-254.
Laemmli UK., Cleavage of Structural Proteins during the Assembly of the Head of Bacteriophage T4. Nature 1970, 227, 680-685.
Invitrogen application notes (http://www.invitrogen.com/site/us/en/home/brands/Product-Brand/Quant-IT.html), printed Feb. 23, 2021.
Invitrogen. Quant-iT™ PicoGreen ® dsDNA Reagent and Kits, Revised: Jun. 10, 2008 | MP 07581.

(Continued)

*Primary Examiner* — Olga N Chernyshev
(74) *Attorney, Agent, or Firm* — K&L Gates LLP

(57) ABSTRACT

The present invention relates to a novel cloning, expression and refolding process for preparing antibody fragments. More particularly, the present invention relates to a cloning, expression and refolding platform for preparing recombinant humanized (rHu) Ranibizumab.

8 Claims, 11 Drawing Sheets

Specification includes a Sequence Listing.

(56) References Cited

OTHER PUBLICATIONS

Rathore A., Bhambure R., Establishing analytical comparability for "biosimilars": filgrastim as a case study. Analytical and Bioanaiyticai Chemistry 2014, 406, 6569-6576.
PCT Search Report and Written Opinion dated Jul. 16, 2018 issued for International PCT Application No. PCT/IN2018/050315.
Singh et al. "Solubilization and refolding of bacterial inclusion body proteins", Journal of Bioscience and Bioengineering, Amsterdam, NL, vol. 99, No. 4, Apr. 2005, pp. 303-310.
Xu et al., Protein Expression and Purification 83 (1): 30-36 (2012).
Donovan, et al., "Optimizing the expression of a monoclonal antibody fragment under the transcriptional control of the *Escherichia coli* lac promoter" Can J. Microbiol. 36: 532-541 (2000).

METHOD FOR PRODUCING REFOLDED RECOMBINANT HUMANIZED RANIBIZUMAB

CROSS-REFERENCE TO RELATED APPLICATIONS

The present application is a continuation-in-part of International PCT Application No. PCT/IN2018/050315 filed on May 18, 2018 which claims priority to Indian Patent Application No. 201711017654 filed on May 19, 2017, the contents of which are incorporated herein by reference for all purposes.

SEQUENCE LISTING

The instant application contains a Sequence Listing which has been filed electronically in ASCII format and is hereby incorporated by reference in its entirety. Said ASCII copy, created on Jan. 15, 2020, is named 0815211_00018_SL.txt and is 6,853 bytes in size.

FIELD OF THE INVENTION

The present invention relates to a novel cloning, expression and refolding process for preparing antibody fragments.

More particularly, the present invention relates to a cloning, expression and refolding platform for preparing recombinant humanized (rHu) Ranibizumab.

BACKGROUND OF THE INVENTION

Time and cost effective manufacturing of target therapeutic proteins is a key component in success of biosimilar industries. Recent trend in biopharmaceutical research and development is more focused on antibody fragment development. Antibody fragments offer certain advantages over full sized monoclonal antibody therapeutics such as improved and deep tumor penetration, specific epitope binding which are not accessible to full size mAb etc.[1-2].

Bacterial expression of small and unglycosylated antibody fragments becomes easier and cheaper than monoclonal antibody production in mammalian cell systems. Ranibizumab is a recombinant humanized monoclonal antibody fragment used wet type age related macular degeneration treatment[3]. It is anti-angiogenic and inhibits the biological activity of human vascular endothelial growth factor A (VEGF A). The humanized monoclonal antibody fragment is conventionally expressed in E. coli cells by recombinant DNA technology and is targeted against human vascular endothelial growth factor A[3, 4].

rHu Ranibizumab contains 214-residue light chain linked by a disulfide bond at its C-terminus to the 231-residue N-terminal segment of the heavy chain[5]. Molecular weight of rHu Ranibizumab is 48,380 Dalton with a heavy chain molecular weight of 24,953 Dalton and a light chain of 23,430 Dalton respectively. rHu Ranibizumab produced using E. coli cells forms inclusion bodies in the form of insoluble protein aggregates.

In terms of rHu Ranibizumab, expressed as inclusion bodies, refolding is a key rate limiting step in the overall manufacturing. Existing commercial refolding processes for this Fab molecule is based on one of the "3D" technique (Dilution or Diafiltration or Dialysis) to convert the aggregated form of the protein into a biologically active soluble form[6-9]. At present there is negligible understanding about in-vivo and in-vitro folding pathway for Ranibizumab preparation. Due to limited understanding and literature available on in-vitro refolding of rHu Ranibizumab, antibody fragments are often expressed in soluble form in E. coli periplasm. However, bacterial periplasm constitutes only 8%-16% of the total cell volume, limiting the amount of expressed soluble protein. Higher level protein expression into the periplasm also leads to inclusion body formation, which severely limits productivity both in terms of quantity of protein produced and time required for production.

Expression into the periplasm compartment of E. coli is the most common manufacturing technique for antibody fragments. Critical drawback of periplasmic expression is lower yield, which makes commercial viability of such processes a difficult task. There exist several reports on the periplasmic expression of antibody fragments in E. coli. Antibody fragment against tetanus toxoid was expressed in periplasmic space by conjugating single sequence with light chain and heavy chain of antibody fragment leading to 16 mg/l yield.

It is worth observing in several prior art disclosures that periplasmic secretion of antibody fragments leads to protein synthesis in minimal yield. Humphreys D P et al demonstrate the production of the antibody fragment of anti-human IgG in E. coli by using dual promoter vector pDPH128. Functional soluble form of this antibody fragment was achieved by periplasmic secretion with 150 mg/l yield. Bovine antibody fragment Fab was produced by using pComBov vector in E. coli HB2151. Expressing this antibody fragment in periplasm resulted in 2 mg/l of overall yield[13]. Periplasmic expression of antibody fragment of HuMAb4D5-8 was achieved in E. coli with 1-2 g/l yield[14]. Periplasmic expression of therapeutic proteins often leads to lower expression levels due to misfolding and aggregation[15].

Patent literature relating to periplasmic expression of antibody fragments and techniques such as tagging used have been employed, however none of the attempts have been able to obtain antibody fragment preparation.

US Patent Publication No. 2016289314 discloses a signal sequence for exporting light chain and heavy chain of rHu Ranibizumab to the periplasmic space of E. coli cells. This patent publication describes a technique for expression of light and heavy chain of rHu Ranibizumab using different expression vectors but employing the same host cell for protein expression in periplasm. Equal proportion of light chain and heavy chain were combined for in vitro refolding by dilution method.

PCT Publication No. WO9845331 discloses humanized and variant anti VEGF antibodies production with properties from a therapeutic perspective including: (a) strong binding affinity for VEGF antigen; (b) ability to inhibit VEGF-induced proliferation of endothelial cells and (c) ability to inhibit VEGF-induced angiogenesis in vivo. The patent application discloses nucleotide sequence of variable light chain and variable heavy chain and expressed by transforming vector containing VL and VH into E. coli cells.

PCT Publication No. WO2013076657 discloses the methionine aminopeptidase (MAP) protein as a fusion tag to obtain a soluble protein of interest in BL21 (DE3) E. coli cells. rHu Ranibizumab light chain and heavy chain gene sequence was tagged with s MAP protein and MAPLC and MAPHC fusion protein were expressed in soluble form.

PH12015501593 (A1) discloses a hybridoma technique for synthesizing anti-VEGF antibody soluble and stable anti-VEGF immuno binders comprising CDRs from rabbit monoclonal antibodies. It further discloses a nucleotide sequence of variable region of light chain and heavy chain and expression constructs for expression of recombinant antibodies fragment. Plasmids expressing scFv or Fab polypeptides are introduced into a suitable host, preferably *E. coli* strain JM83 for periplasmic expression or BL21 for expression in inclusion bodies. The polypeptide can be harvested either from the periplasm or form inclusion bodies and purified using standard techniques such as ion exchange chromatography, reverse phase chromatography, affinity chromatography and/or gel filtration.

US Patent Publication No. 2008125580 discloses a process for purifying refolded recombinant proteins produced in heterologous host cells and refolding the protein in a high pH buffer. Recombinant protein like growth factors such as acidic fibroblast growth factor, basic fibroblast growth factor and vascular endothelial growth factor were expressed in host cells and refolded by addition of buffer containing reducing agent and chaotropic agent along with addition of air or oxygen.

In light of the drawbacks encountered with periplasmic expression of antibody fragments, there is a need in the art to develop a process for the cytoplasmic expression of antibody fragments in equal proportion having improved purity and yield.

OBJECT OF THE INVENTION

The defining object of the present invention is to provide a cloning process for the preparation of antibody fragments.

An object of the present invention is to provide the recombinant constructs carrying nucleotide sequences encoding for heavy chain and light chain of antibody fragments and its equal expression in host cells.

Another object of the present invention is to obtain the cytoplasmic expression of recombinant antibody fragments.

Yet another object of the present invention is to employ high cell density fermentation for economic production of a recombinant antibody fragment.

Yet another object of the present invention to provide a high throughput refolding process for the preparation of recombinant humanized (rHu) Ranibizumab.

SUMMARY OF THE INVENTION

The defining aspect of the present invention is to provide a cloning process for preparing refolded antibody fragments.

In another aspect the present invention provides a cloning process for preparing refolded recombinant humanized antibody fragments, the said method comprising;
(a) transforming vectors carrying nucleotide sequence encoding heavy and light chains of antibody fragments in host cells;
(b) subjecting host cells to high density cell fermentation;
(c) co-expressing light and heavy chains of the said antibody fragments into the host cell cytoplasm in equal proportions by induction in the presence of a mixture comprising glucose and IPTG.

The process for preparing refolded recombinant humanized antibody fragments further comprises;
(i) solubilizing inclusion bodies containing equal proportion of light and heavy chains of recombinant antibody fragments in the presence of a solubilization buffer to obtain solubilized light and heavy chains; and
(ii) refolding the solubilized antibody fragments by diluting a denaturant followed by oxygenation in the presence of an oxidizing agent to trigger oxidation of disulfide bond to obtain biologically active form of rHu Ranibizumab.

In yet another aspect, the present invention provides a cloning and refolding process of recombinant humanized Ranibizumab.

DETAILED DESCRIPTION OF THE INVENTION

The invention will now be described in detail in connection with certain preferred and optional embodiments, so that various aspects thereof may be more fully understood and appreciated.

Source of biological material: *E. coli* BL21 (DE3) cells purchased from Merck Millipore Life Science Private Limited, India.

In a preferred embodiment, the present invention provides a cloning process for preparing refolded recombinant humanized antibody fragments, the said process comprising;
(a) transforming vectors carrying nucleotide sequence encoding heavy and light chains of antibody fragments in host cells;
(b) subjecting host cells to high density cell fermentation, co-expressing light and heavy chains of said antibody fragments into the host cell cytoplasm in equal proportions by induction in the presence of a mixture comprising glucose and IPTG.

The step of 'transforming vectors' in the present invention refers to transforming at least one duet vector carrying nucleotide sequences encoding the heavy and light chain of an antibody fragment in host cells.

In a particular embodiment, the present invention provides a cloning process for preparing refolded recombinant humanized Ranibizumab, the said process comprising;
(i) transforming vectors carrying Seq Id No. 1 and Seq Id No. 3 encoding the heavy chain and light chain of Ranibizumab in host cells;
(ii) subjecting host cells to high density cell fermentation;
(iii) co-expressing light and heavy chains of the said antibody fragments into the host cell cytoplasm in equal proportions by induction in the presence of a mixture comprising glucose and IPTG.

In an embodiment, the present invention provides a nucleotide sequence of Seq Id No. 1 encoding the heavy chain of Ranibizumab of Seq Id No. 2.

In another embodiment, the present invention provides the nucleotide sequence of Seq Id No. 3 encoding the light chain of Ranibizumab of Seq Id No. 4.

In one embodiment, the present invention provides a vector construct carrying Seq Id No. 1 and Seq Id No. 3 for equal expression of heavy chain and light chain of the antibody fragment.

Figure 1:
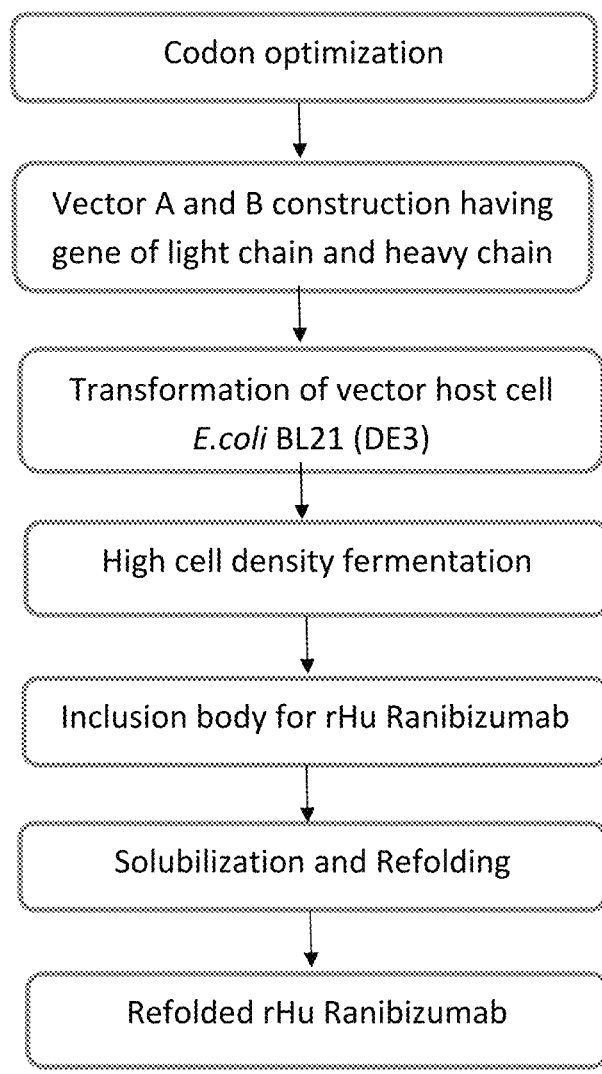
FIG. 1 depicts a novel cloning, expression and refolding platform for rHu Ranibizumab.
Figure 2:
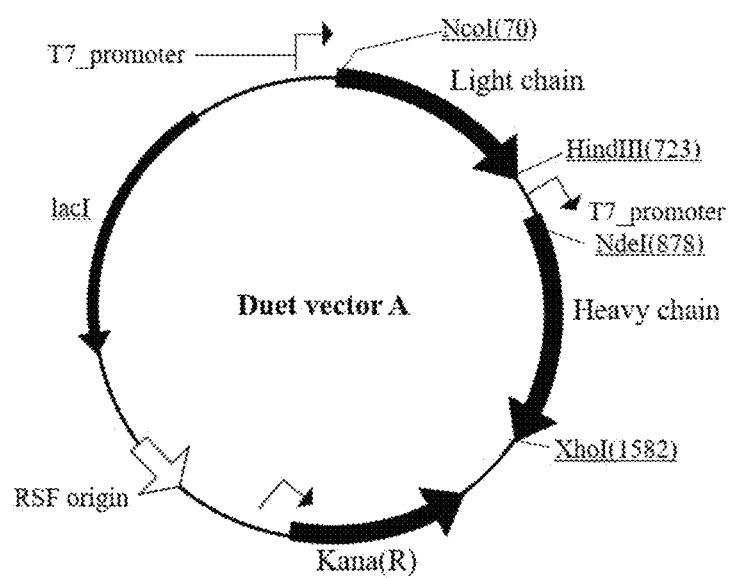
FIG. 2 depicts a Duet vector A for the expression of light and heavy chain gene of a rHu Ranibizumab.

Accordingly, a duet vector comprising nucleotide Seq Id No. 3 encoding light chain of the antibody fragment inserted at 5' end into NcoI/HindIII site preceded by T7 promotor in multiple cloning site I (MCS I) and nucleotide Seq Id No. 1 encoding heavy chain at 5' end into NdeI/XhoI site preceded by T7 promotor in multiple cloning site II (MCS II). (FIG. 2)

Figure 3:
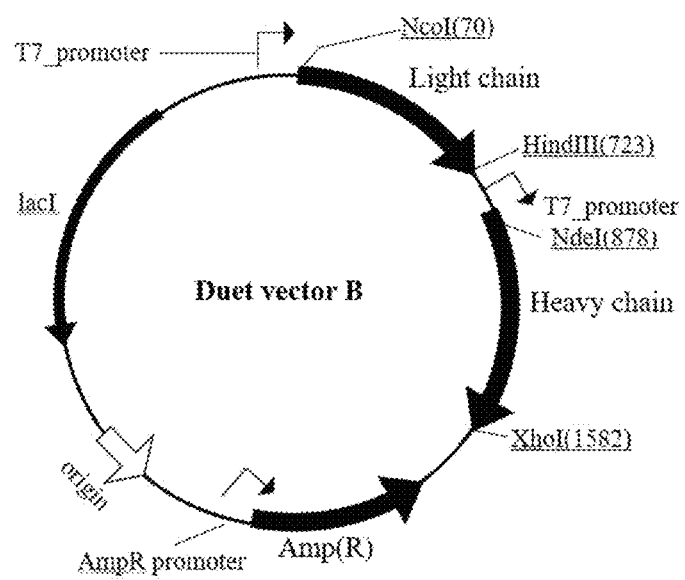
FIG. 3 depicts a Duet vector B for the expression of light and heavy chain gene of a rHu Ranibizumab.

In a further embodiment, the present invention provides a duet vector comprising nucleotide Seq Id No. 3 encoding light chain of the antibody fragment inserted at 5' end into NcoI/HindIII site preceded by T7 promotor in multiple cloning site I (MCS I) and nucleotide Seq Id No. 1 encoding heavy chain at 5' end into NdeI/XhoI site preceded by T7 promotor in multiple cloning site 11 (MCS II). (FIG. 3)

In another preferred embodiment, at least one duet vector carrying light and heavy chain gene construct is transformed in an expression system. The most preferable expression system subjected to transformation is competent *E. coli* BL21 (DE3) cells. Selected transformants of BL21 (DE3) cells were determined for rHu antibody fragment expression.

Figure 4:
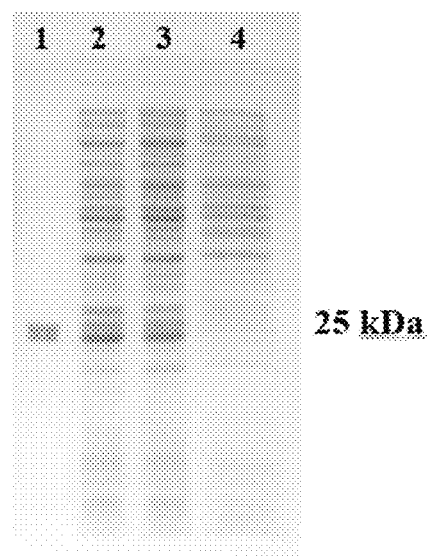
FIG. 4 depicts reducing SDS-PAGE wherein lane 1: Reduced standard innovator rHu Ranibizumab. 2: Light chain and heavy chain gene expression using duet vector A, 3: Light chain and heavy chain gene expression using duet vector B. 4: Uninduced *E. coli* cells.

FIG. 4 shows expression of light chain and heavy chain using duet vector A and duet vector B, which conformed nearly equal expression of both chains without any leaky expression in un-induced *E. coli* host cells. More preferably, consistent and higher level of equal expression of the light chain and heavy chain of rHu Ranibizumab was observed using duet A vector, using 12% reducing SDS-PAGE is exhibited in FIG. 5.

Figure 7:
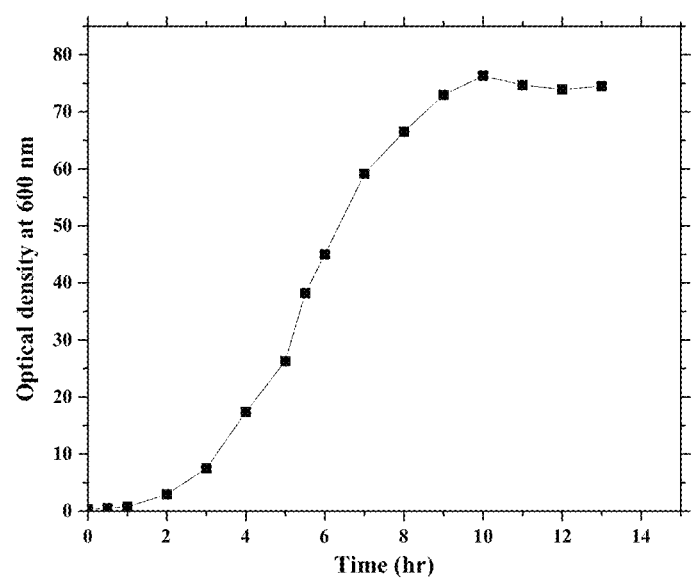
FIG. 7 depicts a growth curve for high cell density *E. coli* fermentation for rHu Ranibizumab production.

In one more embodiment, the present invention provides biomass yield ranging from about 175 g/l to about 190 g/l comprising about 5 g/l to about 15 g/l inclusion body. FIG. 7 shows an increase in the growth rate for transformed *E. coli* cells subjected to high cell density fermentation for rHu Ranibizumab production.

Figure 12:
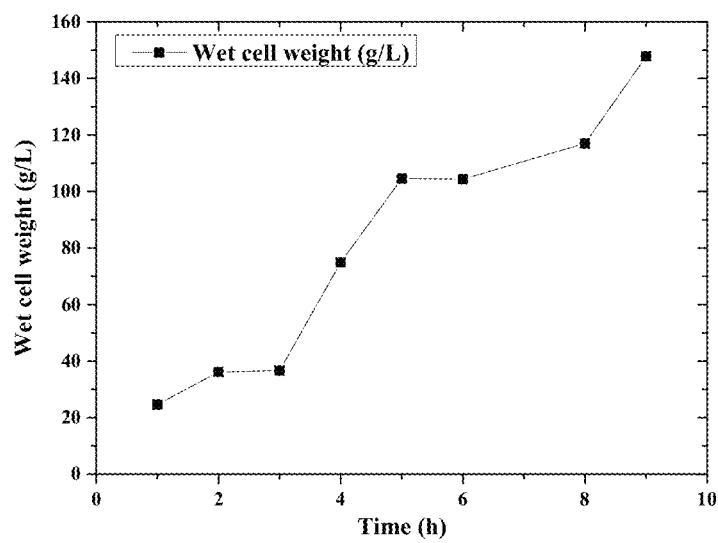
FIG. 12 shows the growth curve for *E. coli*, showing the biomass yield increase with respect to time.

FIG. 12 shows the growth curve for *E. coli*, showing the biomass yield increase with respect to time.

In another preferred embodiment, the present invention provides a process for preparing refolded recombinant humanized antibody fragments further comprising;
(i) solubilizing inclusion bodies containing equal proportion of light and heavy chains of recombinant antibody fragments in a solubilization buffer to obtain solubilized light and heavy chains followed by oxidation; and
(ii) refolding the solubilized antibody fragments by diluting a denaturant followed by oxygenation in the presence of an oxidizing agent to trigger oxidation of disulfide bond to obtain biologically active form of rHu Ranibizumab.

In an embodiment, the present invention provides a solubilization buffer comprising a Tris buffer, EDTA, a denaturant and a reducing agent.

The preferable denaturant is selected from the group consisting of guanidine hydrochloride or urea.

The preferable reducing agent is selected from the group consisting of Dithiothreitol (DTT) or and β-mercaptoethanol.

Accordingly, the preferable concentration of Tris buffer is in the range of 0.1 M to 0.5 M, with pH in the range of 7 to 10. The preferable concentration of EDTA is in the range of 1 mM to 4 mM and that of guanidine hydrochloride is in the range from about 3 mM to about 6 mM.

Most preferably, the solubilization buffer comprises 0.1 M Tris pH 9.0, 2 mM EDTA and 6 M guanidine hydrochloride as a denaturant for 30 min, and further comprises a reducing agent, i.e. 5 mM DTT.

The soluble and reduced inclusion body solution was subjected to oxidation by adding 10 mM oxidized glutathione. Followed by the refolding using 75 fold dilution at 10±2° C. in refolding buffer contained 0.1 M Tris pH 9.0, 0.6 M Arginine, 5% Sorbitol, 2 mM EDTA. Oxidative refolding was also carried out by passing pure oxygen by 1 SLPM (Standard liter per minute) flow rate into in vitro refolding process.

Oxygen triggered the formation of disulfide bond and rate of reaction by oxidation of thiol group in cysteine amino acid. Redox shuffle was also used and it formed a mixed disulfide bond with cysteine amino acid of protein followed by a nucleophilic attack which allowed to form correct disulfide bonds between cysteine amino acids of the protein molecule.

Biologically active refolded functionally active rHu Ranibizumab in the range of 100 to 110 µg/ml was obtained.

Further, a good agreement between innovator rHu Ranibizumab and the developed rHu Ranibizumab with 85.4% of theoretical sequence coverage by peptide finger printing analysis is obtained.

EXAMPLES

Following examples are given by way of illustration therefore should not be construed to limit the scope of the invention.

Example 1: Codon Optimization for Construction of Light Chain and Heavy Chain Gene Sequence The amino acid sequence of the light chain and heavy chain of rHu Ranibizumab was retrieved from drug bank and codon optimization was performed (Accession No.: DB01270).

Example 2: Construction of Duet Vector a for Expression of Light Chain and Heavy Chain of rHu Ranibizumab Duet vector A (FIG. 2) was constructed by inserting light chain nucleotide sequence ID No. 3 at 5' end into NcoI/HindIII cloning site preceding by T7 promotor in multiple cloning site I (MCS I) and heavy chain nucleotide sequence ID No. 1 at 5' end into NdeI/XhoI site preceding by T7 promotor in multiple cloning site II (MCS II).

Example 3: Construction of Duet Vector B for Expression of Light Chain and Heavy Chain of rHu Ranibizumab Duet vector B (FIG. 3) was constructed by inserting light chain nucleotide sequence ID No. 3 at 5' end into NcoI/HindIII site preceding by T7 promotor in multiple cloning site I (MCS I) and heavy chain nucleotide sequence ID No. 1 at 5' end into NdeI/XhoI site preceding by T7 promotor in multiple cloning site II (MCS II).

Example 4: Transformation of Expression Construct in BL21 (DE3) Host Cell

Duet vector A and B having light heavy chain gene construct was transformed in competent BL21 (DE3) expression system. Transformation method comprises[22]: Incubation of 100 μl host cell with 0.5 μg vector for 30 min on ice, followed by a heat shock at 42° C. for 35 seconds. After the heat shock, cells were again incubated on ice for 15 minute. 800 μl of Super Optimal broth with Catabolite repression (SOC) medium was then added to a reaction mix followed by an incubation of 1 hr and 45 minute at 450 rpm. Transformed cells were centrifuged at 2000 rpm for 5 minute. BL21 (DE3) *E. coli* transformants were plated on 30 μg/ml kanamycin containing LB agar plates. Transformed cell containing plates were incubated at 37° C. for overnight. Based on the antibiotic selection marker, positively transformed cells were isolated from the plates and were used for protein expression.

Example 5: rHu Ranibizumab Expression at Shake Flask Level

Figure 5:
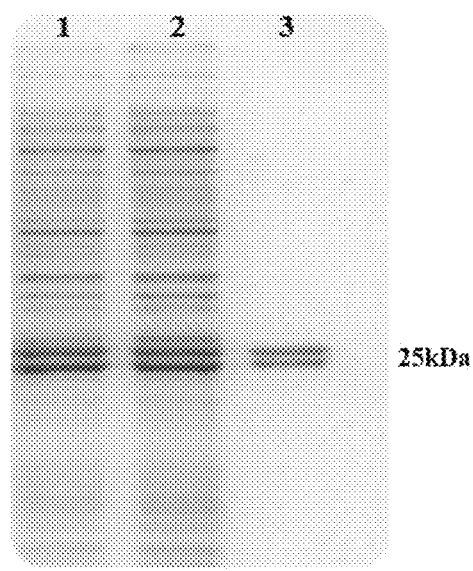
FIG. 5 depicts reducing SDS-PAGE. 1 and 2: Reduced developed rHu Ranibizumab 3: Reduced standard innovator rHu Ranibizumab.
Figure 8:
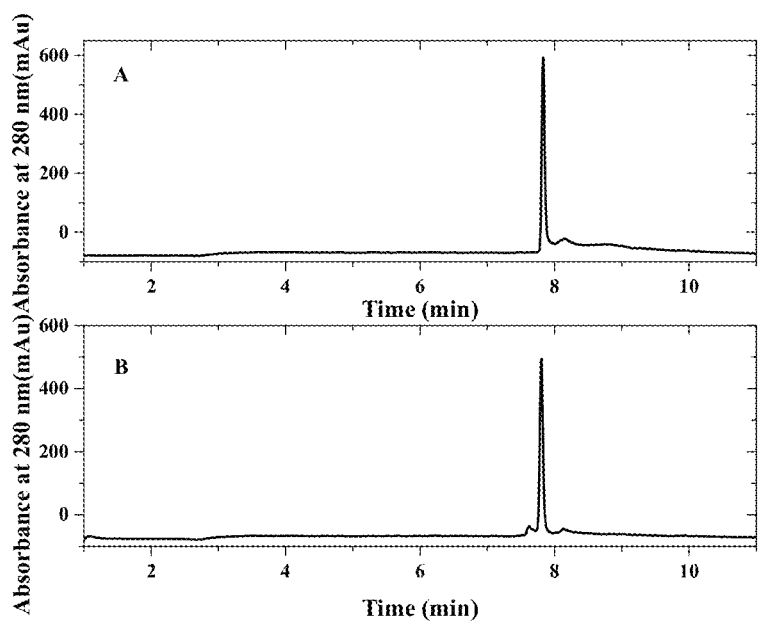
FIG. 8 depicts Reversed phase HPLC chromatogram of refolded rHu Ranibizumab. A: Standard innovator rHu Ranibizumab. B: Refolded rHu Ranibizumab.

Selected transformants of BL21 (DE3) cells were tested for rHu Ranibizumab expression. The selected colonies were inoculated into 10 ml LB broth with 30 μg/ml kanamycin. Cells were grown until the optical density at 600 nm reached the value between 1 to 1.5. 2 ml of these well-grown colonies were transformed into 100 ml Terrific HiVeg™ broth and incubated at 37° C. and 250 rpm. After achieving an optical density of 1-1.-50 at 600 nm the *E. coli* culture was induced with 5 mM IPTG. Cells were harvested after 5 hr induction and centrifuged at 6000 rpm for 20 min. Supernatant was discarded and the cell pellet was resuspended in 20 mM Tris, 0.1 mM EDTA pH 9.0 lysis buffer. Cells were lysed in high pressure homogenizer at 15000 bar pressure for 20 minutes. Lysed cells were centrifuged at 6000 rpm for 25 minutes. Presence of expressed protein in supernatant and pellet was checked using reducing and non-reducing SDS-PAGE analysis. FIG. 4 shows the expression of the light chain and heavy chain using duet vector A and duet vector B, which conformed nearly equal expression of both chains without any leaky expression in uninduced *E. coli* host cells. Higher level equal expression of the light chain and heavy chain of rHu Ranibizumab was observed using duet A vector, using 12% reducing SDS-PAGE (FIG. 5). Shake flask level *E. coli* fermentation lead to an optical density of 3.78±0.05 at 600 nm with 9.3±0.12 g/l biomass leading to generation of 0.868±0.01 g/l inclusion body production. The quantity and purity of light and heavy chain of rHu Ranibizumab in inclusion body was measured by reverse phase HPLC (FIG. 8).

Example 6: rHu Ranibizumab Expression at Bioreactor Level

Protein expression was carried out in a 1 L bioreactor. Selectively transformed BL21 (DE3) cells were evaluated for rHu Ranibizumab expression. The selected colonies were inoculated into 10 ml LB broth with 30 μg/ml kanamycin. Cells were grown until the optical density at 600 nm reached in between 1 to 1.5. 2 ml of these well-grown colonies were transformed into 100 ml of LB broth and incubated it at 37° C. and 250 rpm. 100 ml seed culture was transformed into 900 ml Terrific HiVeg™ broth. High cell density fermentation was carried out by using BioFlo®/CelliGen®115 benchtop fermenter with automatic gas mixture at 1 SLPM gas flow range by using 2 L heat blanketed glass vessels with baffles assembly having direct drive motor, two Rushton impellers and ring sparger (Macrosparger). Automatic DO cascade agitation, GasFlo and the 02 mix was selected with a DO set point of 30%. Agitation cascade lower limit was kept at 300 rpm and the higher limit was kept at 1000 rpm. GasFlo cascade was kept at 1 SLPM and 02 mix was kept 0-80%. *E. coli* culture was induced with 5 mM IPTG at mid-log phase. Cells were harvested after 5 hr of induction and centrifuged it at 6000 rpm for 20 minutes. Supernatant was discarded and the cell pellet was resuspended in 20 mM Tris, 0.1 mM EDTA pH 9.0 lysis buffer. Cells were lysed in high-pressure homogenizer for 20 min at 15000 bar pressure. Lysed cells were centrifuged at 6000 rpm for 25 minutes. Presence of the expressed rHu Ranibizumab in supernatant and pellet was determined using SDS-PAGE analysis. High cell density *E. coli* fermentation lead to optical density of 75.0±1.2 at 600 nm with 182±2.9 g/l biomass leading to the generation of 7.0±0.1 g/l inclusion body production (FIG. 7).

Example 7: Refolding of Protein and Pretreatment for Inclusion Body of Light Chain and Heavy Chain of rHu Ranibizumab Solubilization Protocol:
170 mg wet weight of inclusion bodies were initially solubilized in 10 ml solubilization buffer containing 0.1 M Tris pH 9.0, 2 mM EDTA and 6M Guanidine hydrochloride as a denaturant for 30 min. Reduction was carried out by adding 5 mM DTT and kept it 1 hr for reduction at 25° C. This soluble and reduced inclusion body solution was kept for oxidation by adding 10 mM oxidized glutathione for 3 hr at 25° C.

Figure 6:
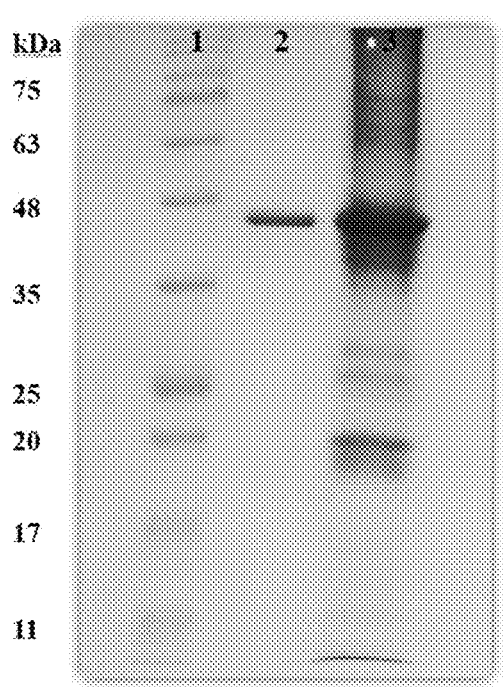
FIG. 6 depicts non reducing SDS-PAGE. 1: Protein molecular weight marker, 2: Standard innovator rHu Ranibizumab. 3: Refolded rHu Ranibizumab.

Refolding Protocol:
This soluble and reduced and oxidized inclusion body was diluted 75 fold at 10±2° C. in the refolding buffer containing 0.1 M Tris pH 9.0, 0.6 M Arginine, 5% Sorbitol, 2 mM EDTA. Oxidative refolding was carried out by passing pure oxygen by 1 SLPM (Standard liter per minute) flow rate into in vitro refolding process. Oxygen triggered the formation of disulfide bond and rate of the reaction by oxidation of thiol group in cysteine amino acid. Redox shuffle was also used and it formed a mixed disulfide bond with cysteine amino acid of protein followed by a nucleophilic attack which allowed to form correct disulfide bonds between cysteine amino acids of the protein molecule. Refolding output was subjected to ultra-filtration by using 5 kDa Ultrasette™ Lab Tangential Flow Filtration devise followed by buffer exchanged into 20 mM Tris pH 9.0. Refolded rHu Ranibizumab was observed on non-reducing 12% SDS-PAGE at 48 kDa (FIG. 6). The quantity and quality of refolded rHu Ranibizumab were measured by reverse phase and size exclusion HPLC (FIG. 8).

Example 8: Analytical Characterization of Recombinant rHu Ranibizumab Absorbance Measurement at A280 for rHu Ranibizumab Samples Total protein in refold and chromatography outputs was determined using UV absorbance measurement at 280 nm. All fractions collected were read at 280 nm using Nanodrop™ 2000 and UV-1800 Shimadzu UV Visible spectrophotometer.

Example 9: Bradford's Assay for Total Protein Estimation for rHu Ranibizumab An orthogonal technique used for the total protein estimation was the Bradford's assay at 595 nm using Nanodrop™ 2000. After adding 5 µl of the sample into 250 µl of Bradford reagent, mixing was performed on the shaker for 30 seconds. After mixing, the sample was incubated in presence of the dye for 25 minutes and absorbance was measured at 595 nm[25].

Example 10: SDS PAGE Analysis of rHu Ranibizumab Samples

SDS PAGE analysis for identification of expression of light chain and heavy chain of rHu Ranibizumab was carried out using 12% (Thickness 1 mm) of the resolving gel under reducing condition (FIG. 4) and refolded rHu Ranibizumab was observed on non-reducing SDS-PAGE (FIG. 7) at the stacking gel constant voltage 120V and resolving gel constant voltage 100V conditions. Each sample was boiled for 10 min in the starting buffer before being loaded into the gel. 0.05% (w/v) Coomassie brilliant blue G-250 in 4:1:5 (Water: Glacial Acetic acid:Methanol) was used to detect proteins after electrophoretic separation on polyacrylamide gels[26].

Example 11: Reverse Phase HPLC Analysis of rHu Ranibizumab

Quantitative and qualitative analysis of rHu Ranibizumab was performed using reverse phase chromatography (FIG. 8) using 4.6 mm×50 mm Poroshell 120 EC-C18 2.7 µm column on Agilent 1260 HPLC system. The mobile phase consisted of 0.1% (v/v) TFA in water (solvent A) and 0.1% (v/v) TFA, 100% (v/v) of acetonitrile (solvent B). Flow rate was maintained at 1 ml/min using a linear gradient of A to B at a wavelength of 214 nm. FIG. 8 shows RP-HPLC chromatogram of innovator and refolded rHu Ranibizumab.

Example 12: ELISA Analysis for Quantification of In-Vitro Bioactivity of rHu Ranibizumab Samples containing refolded rHu Ranibizumab were reacted with VEGF antigen coated on the plate. Bounded rHu Ranibizumab detected by horseradish peroxidase (HRP) enzyme labeled anti human IgG. The immunological reactions result in the formation of a sandwich complex of solid phase VEGF bounded antibody-Ranibizumab-enzyme labeled antibody. The microtiter strips are washed to remove any unbound reactants. The substrate, tetramethyl benzidine (TMB) is then reacted. The amount of hydrolyzed substrate is read on a microtiter plate reader at 450 nm and is directly proportional to the concentration of rHu Ranibizumab present. Biologically active refolded rHu Ranibizumab was quantify using in vitro bioassay. 102 µg/ml functionally active rHu Ranibizumab was obtained[27].

Example 13: SE HPLC Analysis of rHu Ranibizumab

Figure 9:
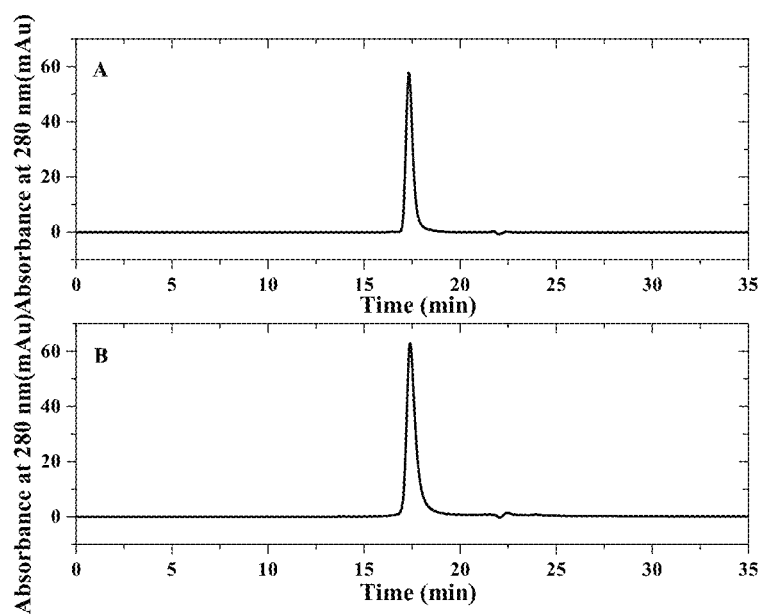
FIG. 9 depicts Size exclusion chromatogram of refolded rHu Ranibizumab. A: Standard innovator rHu Ranibizumab. B: Refolded rHu Ranibizumab.

Aggregate content in the various process outputs was determined using SEC-HPLC analysis (FIG. 9) performed using Yarra™ 3 µm SEC-2000(300×7.8 mm ID) column. The mobile phase consists of 20 mM acetate buffer with 50 mM sodium chloride buffer at pH 5.50. Analysis was done in isocratic mode with 0.5 ml/min flow rate at 25° C. Protein detection was done using photo diode array detector at 280 nm. FIG. 9 shows 99.5% purity of purified rHu Ranibizumab comparable with innovator rHu Ranibizumab with 0.5% aggregates content.

Example 14: Double Stranded DNA Estimation

Presence of DNA in the refolding output was estimated using Quant-iT™ picogreen assay. Standard curve was prepared using double stranded lambda DNA. 0.5 ml of the process output sample was added to the 0.5 ml of diluted Quant-iT™ dsDNA BR reagent and the reaction mixture was incubated for 5 minutes. After five minute fluorescence was measured using fluorescence spectrophotometer (excitation wavelength 480 nm and emission wavelength 520 nm).

Example 15: Intact Mass Analysis of Refolded rHu Ranibizumab by Matrix-Assisted Laser Desorption/Ionization (MALDI-TOF) (Time-of-Flight Mass Spectrometer)

Figure 10:
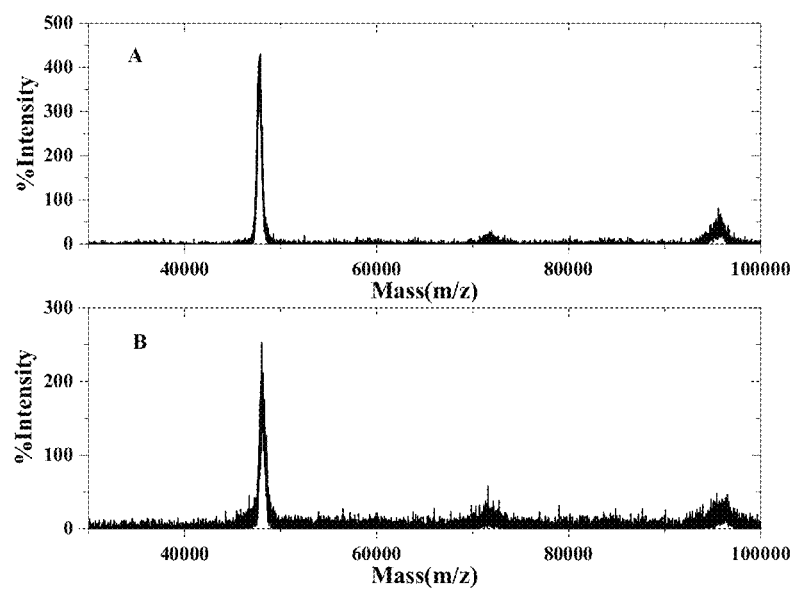
FIG. 10 depicts intact mass analysis of rHu Ranibizumab by MALDI-TOF. A: Standard innovator rHu Ranibizumab, B: Refolded rHu Ranibizumab.
Figure 11:
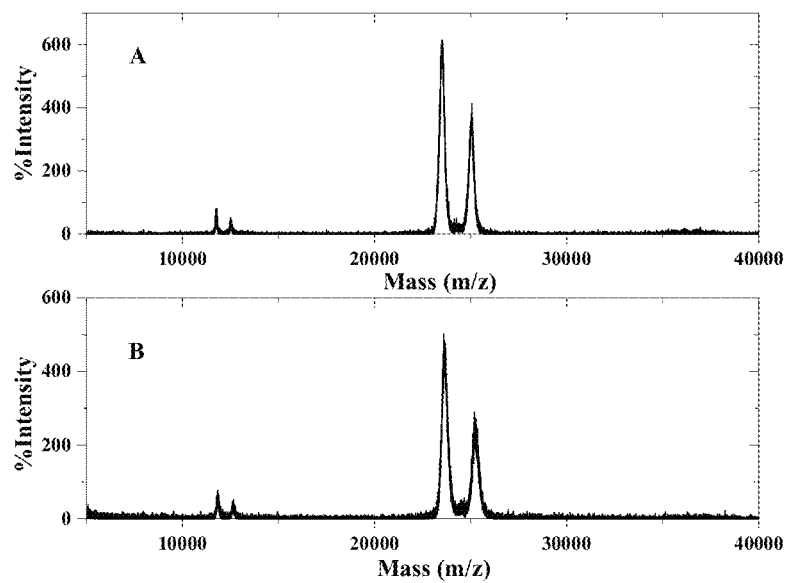
FIG. 11 depicts Reduced and alkylated rHu Ranibizumab mass analysis by MALDI-TOF. A: Standard innovator rHu Ranibizumab light chain and heavy chain B: Developed rHu Ranibizumab light chain and heavy chain.

Standard and refolded purified rHu Ranibizumab with sinapinic acid matrix was mixed in 1:1 ratio to perform MALDI-TOF analysis (FIG. 11). Similarly, reduced and alkylated standard and refolded rHu Ranibizumab was mixed with sinapinic acid matrix in 1:1 ratio to perform MALDI-TOF analysis (FIG. 12). Matrix sinapinic acid (10 mg/mL) was prepared in 50% v/v acetonitrile, 0.1% v/v TFA in high purity water. 1 µl of the homogenized mixture of sample and matrix was deposited on a clean 384 well MALDI plate. The plate was inserted into AB SCIEX TOF/TOF™ 5800 instrument. Instrument was used in positive ion mode. Nitrogen laser at 337 nm radiation was kept as an ionization source. Laser intensity in between 4000 to 5000 was used for the analysis of samples. Result analysis was performed using Data Explorer© Software Version 4.11. FIG. 10 shows a comparison of the intact mass of refolded rHu Ranibizumab with innovator rHu Ranibizumab. FIG. 11 shows light chain and heavy chain of purified rHu Ranibizumab mass comparability with reduced and alkylated innovator rHu Ranibizumab.

Example 16: Peptide Fingerprinting by LC-MS

Peptide mapping was achieved by in solution digestion of Bovine serum albumin (BSA), standard innovator rHu Ranibizumab and refolded rHu Ranibizumab. Denaturation of protein was carried out by using 6.0 M guanidine hydrochloride in room temperature for 1 hr. 10 mM of DTT was added for the reduction of denatured protein and incubated for 1 hr in room temperature. Alkylation was carried by using 15 mM iodoacetamide (IAA) and incubated for 15 min in dark condition and again 5 mM DTT was added to neutralize excessive IAA. Denatured, reduced and alkylated protein sample was buffer exchanged in 50 mM ammonium bicarbonate. Trypsin was used for digestion of the protein sample in the ratio of 1:50 (Trypsin: protein). The digestion mix was incubated at 37° C. for 18 hr followed by sample clean up using Ziptip® pipette tips. Cleaned up samples were dried using SPD1010 Speedvac™ concentrator. Digested protein sample was reconstituted in 3% acetonitrile and 0.1% formic acid in mass grade water. Peptide fingerprinting was performed using AB SCIEX TripleTOF™ 5600 System data was recorded and analyzed using ProteinPilot™ software. Results shows a good agreement between the innovator rHu Ranibizumab and the developed rHu Ranibizumab with 85.4% of theoretical sequence coverage[29].

Advantages of the Invention

Equal Expression of light chain and heavy chain is obtained by employing the vector constructs disclosed in the present invention, the stages of manual processing to obtain equal expression of light and heavy chain of the mAb fragment is excluded;

Cytoplasmic expression rather than periplasmic expression of recombinant antibody fragments results in high biomass yield, therefore resulting in increased yield of the recombinant protein.

High cell density fermentation used in the present invention provides for increase in biomass production.

REFERENCES

1. Nelson A. and Reichert J. Development trends for therapeutic antibody fragments. Nature biotechnology 2009, 27, number 4
2. Nelson A., Antibody fragments Hope and hype. MAbs, 2010, 2:1, 77-83.
3. Product insert and prescribing information for Lucentis. (http://www.lucentis.com/information/wet-age-related-macular-degeneration accessed on 141216)
4. EMEA scientific discussion. Website: http://www.ema.europa.eu/docs/en_GB/document_library/EPAR_-_Scientific_Discussion/human/000715/WC500043550.pdf)
5. Ranibizumab drug bank information. (http://www-.drugbank.ca/drugs/db01270).
6. Clark E D B., Protein refolding for industrial processes. Current Opinion in Biotechnology, 2001, 12(1): 202-207.
7. Jungbauer A., Kaar W., Current status of technical protein refolding. Journal of Biotechnology, 2007, 128(3): 587-596.
8. Middelberg A P J., Preparative protein refolding. Trends in Biotechnology, 2002, 20(10), 437-443
9. Singh S. M., Panda A. K., Solubilization and refolding of bacterial inclusion body proteins. Journal of Bioscience and Bioengineering, 2005, 99(4), 303-310.
10. Hannig G. and Makrides S. Strategies for optimizing heterologous protein expression in *Escherichia coli*. Trends in Biotechnology, 1998, 16, 54-60
11. Corisdeo S. and Wang B. Functional expression and display of an antibody Fab fragment in *Escherichia coli*: study of vector designs and culture conditions. Protein Expression and Purification 2004, 34, 270-279
12. Humphreys D., Carrington B., Bowering L., Ganesh R., Sehdev M., Smith B., King L., Reeks D, Lawson A and Popplewell A. A plasmid system for optimization of Fab production in *Escherichia coli*: importance of balance of heavy chain and light chain synthesis. Protein Expression and Purification 2002, 26, 309-320
13. O'Brien Ph., Maxwell G., and Campo M. Bacterial Expression and Purification of Recombinant Bovine Fab Fragments. Protein Expression and Purification 2002, 24, 43-50
14. Carter P., Kelley R., Rodrigues M., Snedecor B., Covarrubias M., Velligan M., Wong W., Rowland A., Kotts C., Carver M., Yang M., Bourell J., Shepard H. and Henner D. High Level *Escherichia coli* Expression and Production of a Bivalent Humanized Antibody Fragment. Nature Biotechnology 1992, 10, 163-167
15. Baneyx F. Recombinant protein expression in *Escherichia coli*. Current Opinion in Biotechnology, 1999, 10, 411-421
16. Shandilya H, Gadgil H. and Farkade V. Cloning, expression & purification method for the preparation of Ranibizumab. 2016, US 20160289314 A1
17. Manuel B., James W., Presta A, Leonard G., Henry, B. and Man Yee Y., Anti-VEGF antibodies. 1998, WO9845331 (A2)
18. Salunkhe Sh., Sriram P. and Kumar J. Map fusion protein. 2013, WO2013076657 (A1)
19. Borras L., Urech D. and Gunde T. Stable and soluble antibodies inhibiting VEGF. 2015, PH12015501593 (A1)
20. Liu N., Song L. and Zhao W., Method for purifying and preparing anti-VEGF antibody fragment, 2012, CN102757496 (A)
21. Pizarro S H., Sanchez A. and Schmelzer C H. Refolding of Recombinant Proteins US2008125580 (A1)
22. User protocol for transformation Novagen® (https://www2.warwick.ac.uk/fac/sci/chemistry/research/bugg/bugggroup/protocols/cloning/tb009_novagen_competent_cells_protocol.pdf) access on 27 Feb. 2017.
23. Buchner J., Rudolph R., Renaturation, purification and characterization of recombinant Fab-fragments produced in *Escherichia coli*. Nature Biotechnology 1991, 9, 157-162
24. Lilie H., Schwarz E., Rudolph R., Advances in refolding of proteins produced in *E. coli*. Current Opinion in Biotechnology 1998, 9, 497-501
25. Bradford M., A rapid and sensitive method for the quantitation of microgram quantities of protein utilizing the principle of protein-dye binding. Analytical Biochemistry 1976, 72, 248-254
26. Laemmli U K., Cleavage of Structural Proteins during the Assembly of the Head of Bacteriophage T4. Nature 1970, 227, 680-685
27. Alpha diagnostic international(http://www.4adi.com/commerce/ccp28617-lucentis-ranibizumab-elisa-kit-for-human--96-test-elisa-kit-200-880-lug.htm) accessed on Sep. 12, 2016.
28. Invitrogen application notes (http://www.invitrogen-.com/site/us/en/home/brands/Product-Brand/Quant-iT.html).
29. Rathore A., Bhambure R., Establishing analytical comparability for "biosimilars": filgrastim as a case study. Analytical and Bioanalytical Chemistry 2014, 406, 6569-6576.

We claim:

1. A method for producing refolded recombinant humanized Ranibizumab, the method comprising:
   (a) transforming vectors carrying nucleotide sequence having SEQ ID No: 1 and SEQ ID No: 3 encoding heavy chain and light chain of antibody fragments in host cells;
   (b) subjecting the host cells to high density cell fermentation;
   (c) co-expressing the light and heavy chains of said antibody fragment into the host cell cytoplasm in equal proportions by induction in the presence of mixture comprising glucose and IPTG to obtain inclusion bodies;
   (d) solubilizing the inclusion bodies containing equal proportions of the light and heavy chains of recombinant antibody fragments in the presence of a solubilization buffer to obtain solubilized light and heavy chains of antibody fragments;
   (e) refolding the solubilized light and heavy chains of antibody fragments by diluting a denaturant followed by oxygenation in the presence of an oxidizing agent to trigger oxidation of disulfide bond to obtain biologically active form of rHu Ranibizumab; and
   (f) subjecting the rHu Ranibizumab obtained in step (e) to ultra-filtration by using 5 KDa tangential flow filtration device followed by 20 mM Tris pH 9.0 to obtain a purified refolded rHu Ranibizumab.

2. The method as claimed in claim 1, wherein the solubilization is carried out using a solubilization buffer comprising 0.1 M Tris buffer pH 9.0, 2 mM EDTA, a denaturant and a reducing agent.

3. The method as claimed in claim 2, wherein the denaturant is selected from the group consisting of guanidine hydrochloride or urea.

4. The method as claimed in claim 2, wherein the reducing agent is selected from the group consisting of Dithiothreitol (DTT) or β-mercaptoethanol.

5. The method as claimed in claim 1, wherein the solubilized light and heavy chains of antibody fragments is subjected to oxidation by adding 10 mM oxidized glutathione followed by passing pure oxygen by 1 SLPM (standard liter per minute) flow rate into an in-vitro refolding process.

6. The method as claimed in claim 1, wherein the refolding is carried out by using refolding buffer comprising 0.1M Tris pH 9.0, 0.6 M Arginine, 5% Sorbitol, 2 mM EDTA.

7. A duet (bicistronic) vector expression system for the expression of light and heavy chain gene of rHu Ranibizumab, wherein the duet vector comprises nucleotide sequence encoding light chain SEQ ID No: 3, nucleotide sequence encoding heavy chain: SEQ ID No: 1, promoter sequence and restriction sites.

8. A method for producing refolded recombinant humanized Ranibizumab, the method comprising:
   (a) transforming duet (bicistronic) vectors carrying nucleotide sequence having SEQ ID No: 1 and SEQ ID No: 3 encoding heavy chain and light chain of antibody fragments in host cells with same promotors both of which are T7 promoters;
   (b) subjecting the host cells to high density cell fermentation;
   (c) co-expressing the light and heavy chains of said antibody fragment into the host cell cytoplasm in equal proportions by induction in the presence of mixture comprising glucose and IPTG to obtain inclusion bodies;
   (d) solubilizing the inclusion bodies containing equal proportions of the light and heavy chains of recombinant antibody fragments in the presence of a solubilization buffer to obtain solubilized light and heavy chains of antibody fragments;
   (e) refolding the solubilized light and heavy chains of antibody fragments by diluting a denaturant followed by oxygenation using pure oxygen in the presence of an oxidizing agent to trigger oxidation of disulfide bond to obtain biologically active form of rHu Ranibizumab; and
   (f) subjecting the rHu Ranibizumab obtained in step (e) to ultra-filtration by using 5 KDa tangential flow filtration device followed by 20 mM Tris pH 9.0 to obtain a purified refolded rHu Ranibizumab.

* * * * *

SEQUENCE LISTING

<160> NUMBER OF SEQ ID NOS: 4

<210> SEQ ID NO 1
<211> LENGTH: 721
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gagctcatat ggaagttcag ctggttgaaa gcggtggtgg tctggttcag cctggtggta      60
gcctgcgtct gagctgtgca gcaagcggtt atgattttac ccattatggt atgaattggg     120
ttcgtcaggc accgggtaaa ggtctggaat gggttggttg gattaatacc tataccggtg     180
aaccgaccta tgcagcagat tttaaacgtc gttttacctt tagcctggat accagcaaaa     240
gcaccgcata tctgcagatg aatagcctgc gtgcagagga taccgcagtg tattattgtg     300
caaaatatcc gtattattac ggcaccagcc attggtattt cgatgtttgg ggtcagggca     360
ccctggttac cgttagcagc gcaagcacca aaggtccgag cgttttccg ctggcaccga     420 gcagcaaaag taccagcggt ggcaccgcag cactgggttg tctggttaaa gattattttc     480
cggaaccggt taccgtgagc tggaatagcg gtgcactgac cagcggtgtt catacctttc     540
cggcagttct gcagagcagc ggtctgtata gcctgagcag cgttgttacc gttccgagca     600
gcagcctggg cacccagacc tatatttgta atgttaatca taaaccgagc aataccaaag     660
tggataaaaa agtggaaccg aaaagctgcg ataaaaccca tctgtaatag ctcgagccgc     720
g                                                                     721
```

<210> SEQ ID NO 2
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide sequence of heavy chain of Ranibizumab

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

```
Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
        210                 215                 220

Ser Cys Asp Lys Thr His Leu
225                 230

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gagctccatg gatattcagc tgacccagag cccgagcagc ctgagcgcaa gcgttggtga        60
tcgtgttacc attacctgta gcgcaagcca ggatattagc aattatctga attggtatca       120
gcagaaaccg ggtaaagcac cgaaagtgct gatctatttt accagcagcc tgcatagcgg       180
tgttccgagc cgttttagcg gtagcggtag tggcaccgat tttaccctga ccattagcag       240
cctgcagccg gaagattttg caacctatta ttgtcagcag tatagcaccg ttccgtggac       300
ctttggtcag ggcaccaaag ttgaaattaa acgtaccgtt gcagcaccga gcgttttttat      360 ctttccgcct agtgatgaac agctgaaaag cggcaccgca agcgttgttt gtctgctgaa       420
taacttttat ccgcgtgaag caaaagttca gtggaaagtt gataatgcac tgcagagcgg       480
taatagccaa gaaagcgtta ccgaacagga tagcaaagat agcacctata gcctgagcag       540 cacccctgacc ctgagcaaag cagattatga aaaacacaaa gtgtatgcct gcgaagttac       600
ccatcagggt ctgagcagtc cggttaccaa aagtttaat cgtggtgaat gctaatagaa        660
gcttggtac                                                               669

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide sequence of Light chain of Ranibizumab

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95
```

-continued

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```